US012002552B2

(12) United States Patent
Ramprasad et al.

(10) Patent No.: US 12,002,552 B2
(45) Date of Patent: Jun. 4, 2024

(54) SYSTEMS AND METHODS FOR PREDICTION OF POLYMER PROPERTIES

(71) Applicant: Georgia Tech Research Corporation, Atlanta, GA (US)

(72) Inventors: Rampi Ramprasad, Atlanta, GA (US); Anand Chandrasekaran, Atlanta, GA (US); Chiho Kim, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 486 days.

(21) Appl. No.: 17/604,621

(22) PCT Filed: Apr. 16, 2020

(86) PCT No.: PCT/US2020/028449
§ 371 (c)(1),
(2) Date: Oct. 18, 2021

(87) PCT Pub. No.: WO2020/214774
PCT Pub. Date: Oct. 22, 2020

(65) Prior Publication Data
US 2022/0044769 A1    Feb. 10, 2022

Related U.S. Application Data

(60) Provisional application No. 62/836,129, filed on Apr. 19, 2019.

(51) Int. Cl.
*G16C 60/00* (2019.01)
*G06N 3/08* (2023.01)
(Continued)

(52) U.S. Cl.
CPC ............... *G16C 60/00* (2019.02); *G06N 3/08* (2013.01); *G16C 20/30* (2019.02); *G16C 20/70* (2019.02)

(58) Field of Classification Search
None
See application file for complete search history.

(56) References Cited

U.S. PATENT DOCUMENTS 6,477,516 B1 *  11/2002  Colaiocco ............... G01N 33/28
                                                    324/303
2010/0332433 A1  12/2010  Lewalle

OTHER PUBLICATIONS

International Search Report and Written Opinion from Application No. PCT/US2020/028449 dated Jul. 15, 2020.
(Continued)

*Primary Examiner* — Giovanni Astacio-Oquendo
*Assistant Examiner* — Carl F. R. Tchatchouang
(74) *Attorney, Agent, or Firm* — Bryan W. Bockhop; Bockhop Intellectual Property Law, LLC (57) ABSTRACT

Disclosed herein is a polymer prediction system, comprising a deep learning neural network and a training dataset. The deep learning neural network can comprise: a property branch comprising two or more layers, each layer having a plurality of neurons; a polymer branch comprising two or more layers, each layer having a plurality neurons; and a merged layer including a concatenation operation, the concatenation operation configured to concatenate the property branch and the polymer branch. The training dataset can include a plurality of known polymers and a plurality of descriptors for each of the plurality of known polymers. Also disclosed herein are methods of using the same.

20 Claims, 5 Drawing Sheets

(51) Int. Cl.
*G16C 20/30* (2019.01)
*G16C 20/70* (2019.01)

(56) References Cited

OTHER PUBLICATIONS

Zeng, et al., "Graph Convolutional Neural Networks for Polymers Property Prediction," arXiv.org Nov. 15, 2018.
"Convolutional Neural Network," Wikipedia 1988 <https://en.wikipedia.org/wiki/Convolutional_Neural_network>.
"Artifical Neural Network," Wikipedia Jan. 2019 <https://en.wikipedia.org/wiki/Artificial_Neural_Network>.
Chandrasekaran, et al., "A Deep Learning Solvent-Selection Paradigm Powered by a Massive Solvent/Nonsolvent Database for Polymers," ACS Publications https://doi.org/10.1021/acs.macromol.0c00251.s001.

* cited by examiner

SYSTEMS AND METHODS FOR PREDICTION OF POLYMER PROPERTIES

CROSS-REFERENCE TO RELATED APPLICATIONS

This application claims the benefit of U.S. Provisional Application Ser. No. 62/836,129, filed on 19 Apr. 2019, the entire contents and substance of which is incorporated herein by reference in its entirety as if fully set forth below.

FIELD OF THE DISCLOSURE

The present disclosure relates generally to systems and methods for predicting polymer properties. Particularly, embodiments of the present disclosure relate to systems and methods for predicting polymer solubility.

BACKGROUND

Polymers are a ubiquitous class of materials and find wide-spread applications in a number of technological and research endeavors. Due to their immense chemical and structural diversity, they are utilized in an unimaginable number of products ranging from bulletproof vests to intricate drug delivery systems. However, this very same diversity renders it difficult to systematically search for polymers possessing specific properties. More recently, the nascent field of polymer informatics has shown promise in accelerating the rational design of novel and functional polymers. For example, one important factor in the synthesis and processing of polymers is the selection of suitable solvents. The compatibility of polymers and solvents is of paramount importance for applications such as paint and coating formulations, plastics, recycling, drug delivery, membrane science, and micro-lithography. In some cases, in order to precipitate a particular polymer from a solution, a non-solvent can be used. For a newly synthesized polymer, it is usually a very time-consuming process to find a proper solvent and/or non-solvent.

What is needed, therefore, are novel frameworks for systems and methods to address the complex problem of polymer property prediction that can continuously evolve with the ever-progressing field of polymer science. Embodiments of the present disclosure address this need as well as other needs that will become apparent upon reading the description below in conjunction with the drawings.

BRIEF SUMMARY OF THE INVENTION

The present disclosure relates generally to systems and methods for predicting polymer properties. Particularly, embodiments of the present disclosure relate to systems and methods for predicting polymer solubility, which may be generalized to predicting other properties as described herein. An exemplary embodiment of the present disclosure can provide a method for predicting polymer properties, the method comprising: submitting, to a polymer prediction system, a first polymer having a first set of functional groups; analyzing the first polymer using a deep learning neural network to analyze the first set of functional groups, the deep learning neural network comprising a property branch, a polymer branch, and a merged layer, wherein the property branch and the polymer branch are concatenated to form the merged layer; determining a value from the merged layer, the value indicative of a property of the first polymer; and outputting the value to a user of the polymer prediction system.

In any of the embodiments disclosed herein, the property branch can be a solubility branch and the property can be a solubility of the first polymer in a first solvent.

In any of the embodiments disclosed herein, the value can be indicative of the first solvent being a good solvent.

In any of the embodiments disclosed herein, the value can be indicative of the first solvent being a nonsolvent.

In any of the embodiments disclosed herein, the determining can further comprise determining that the value is above a predetermined threshold.

In any of the embodiments disclosed herein, the determining can further comprise determining that the value is below a predetermined threshold.

In any of the embodiments disclosed herein, the method can further comprise training the deep learning neural network using a training dataset comprising a plurality of known polymers and a plurality of descriptors for each of the plurality of known polymers.

In any of the embodiments disclosed herein, the property branch can comprise two or more layers, each layer having from 1 to 100 neurons.

In any of the embodiments disclosed herein, the polymer branch can comprise two or more layers, each layer having from 1 to 100 neurons.

In any of the embodiments disclosed herein, the two or more layers can be constructed with a parameterized rectified linear unit.

In any of the embodiments disclosed herein, the merged layer can comprise a sigmoid activation function.

Another embodiment of the present disclosure can provide a polymer prediction system, comprising: a deep learning neural network, comprising: a property branch comprising two or more layers, each layer having a plurality of neurons; a polymer branch comprising two or more layers, each layer having a plurality neurons; and a merged layer including a concatenation operation, the concatenation operation configured to concatenate the property branch and the polymer branch; and a training dataset comprising a plurality of known polymers and a plurality of descriptors for each of the plurality of known polymers.

In any of the embodiments disclosed herein, the system can be configured to: receive an inputted first polymer having a first set of functional groups; analyze the first polymer using the deep learning neural network; determine a value for the first polymer, the value being indicative of a property of the first polymer; and output the property and the value to a user of the polymer prediction system.

In any of the embodiments disclosed herein, the property branch can be a solubility branch and the property can be a solubility of the first polymer in a first solvent.

In any of the embodiments disclosed herein, the value can be indicative of the first solvent being a good solvent.

In any of the embodiments disclosed herein, the value can be indicative of the first solvent being a nonsolvent.

In any of the embodiments disclosed herein, the system can be further configured to determine that the value is above a predetermined threshold.

In any of the embodiments disclosed herein, the system can be further configured to determine that the value is below a predetermined threshold.

In any of the embodiments disclosed herein, each of the two or more layers in the property branch can be constructed with a parameterized rectified linear unit.

In any of the embodiments disclosed herein, each of the two or more layers in the polymer branch can be constructed with a parameterized rectified linear unit.

In any of the embodiments disclosed herein, the deep learning neural network can have a latent space dimensionality from 1 to 10 greater than the Hildebrand and Hansen solubility criteria.

In any of the embodiments disclosed herein, the merged layer can further comprise a sigmoid activation function.

These and other aspects of the present invention are described in the Detailed Description of the Invention below and the accompanying figures. Other aspects and features of embodiments of the present invention will become apparent to those of ordinary skill in the art upon reviewing the following description of specific, exemplary embodiments of the present invention in concert with the figures. While features of the present invention may be discussed relative to certain embodiments and figures, all embodiments of the present invention can include one or more of the features discussed herein. Further, while one or more embodiments may be discussed as having certain advantageous features, one or more of such features may also be used with the various embodiments of the invention discussed herein. In similar fashion, while exemplary embodiments may be discussed below as device, system, or method embodiments, it is to be understood that such exemplary embodiments can be implemented in various devices, systems, and methods of the present invention.

BRIEF DESCRIPTION OF THE DRAWINGS

The accompanying drawings, which are incorporated in and constitute a part of this specification, illustrate multiple embodiments of the presently disclosed subject matter and serve to explain the principles of the presently disclosed subject matter. The drawings are not intended to limit the scope of the presently disclosed subject matter in any manner.

DETAILED DESCRIPTION

As described above, a current problem in the field of polymer science is the difficult and time-consuming process to determine the properties of new polymers. The nascent field of polymer informatics has shown promise in accelerating the rational design of novel and functional polymers. High-throughput computations, in conjunction with an ever-increasing accumulation of experimental measurements, have allowed cutting edge machine-learning algorithms to aid in the construction of prediction models and the discovery of hidden structure-property relationships and trends.

A number of quantitative and heuristic measures have been used in the past to aid in the difficult process of polymer property prediction. For instance, for the process of solvent selection, the Hildebrand criteria is the most well-established and well-known of the so-called solubility parameters. Solubility parameters are based on the concept of "like dissolves like," and when a polymer and solvent possess similar values of the Hildebrand solubility parameter, the solvent is designated as a good solvent for that particular polymer. The one-component Hildebrand parameter is derived from the cohesive energy density of the polymeric/molecular system, and it has been shown to perform reasonably well for non-polar systems without hydrogen bonding. However, this method completely fails in enabling suitable solvent predictions for polar systems with hydrogen bonding.

The phenomenon of polymer/solvent compatibility is contingent on a multitude of chemical, thermodynamic, kinetic, and morphological factors. In order to attempt to capture the multi-dimensional nature of this problem, the 3-dimensional Hansen solubility parameter system was developed. This approach involves the decomposition of the Hildebrand parameter into dispersion, polar, and hydrogen bonding components. However, the Hansen parameter is only available for a handful of polymers and offers only marginal improvement in prediction accuracy (relative to the Hildebrand approach). Quantifying such a complex phenomenon using a limited number of manually fitted, heuristic parameters has proven to be an exceptionally challenging endeavor.

Disclosed herein are polymer property prediction systems and methods. For instance, disclosed herein is a novel paradigm in which polymer-solvent compatibility can be determined using a data-driven framework in contrast to existing heuristic approaches based on solubility parameters. The disclosed systems and methods can utilize a massive dataset of over 4,500 polymers and their corresponding solvents and non-solvents. The dataset can train a deep learning neural network binary classifier which can take the polymer and solvent descriptors as an input. The neural network can then output whether the solvent is a good solvent or a non-solvent for the inputted polymer. In addition to the vastly improved prediction accuracy, the disclosed systems and methods can enable the visualization of solvents and polymers in terms of chemically relevant low-dimensional latent-space vectors. Such latent-space representations can be obtained intrinsically via the machine learning algorithms, without the need to input any empirical or manually derived parameters.

Therefore, the disclosed systems and methods can provide improved polymer property prediction. The present disclosure can provide novel frameworks to address the complex problem of polymer property prediction that can continuously evolve with the ever-progressing field of polymer science.

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. Other embodiments of the disclosure are capable of being practiced or carried out in various ways. Also, in describing the embodiments, specific terminology will be resorted to for the sake of clarity. It is intended that each term contemplates its broadest meaning as understood by those skilled in the art and includes all technical equivalents which operate in a similar manner to accomplish a similar purpose.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter.

Reference will now be made in detail to exemplary embodiments of the disclosed technology, examples of which are illustrated in the accompanying drawings and disclosed herein. Wherever convenient, the same references numbers will be used throughout the drawings to refer to the same or like parts.

Figure 1:
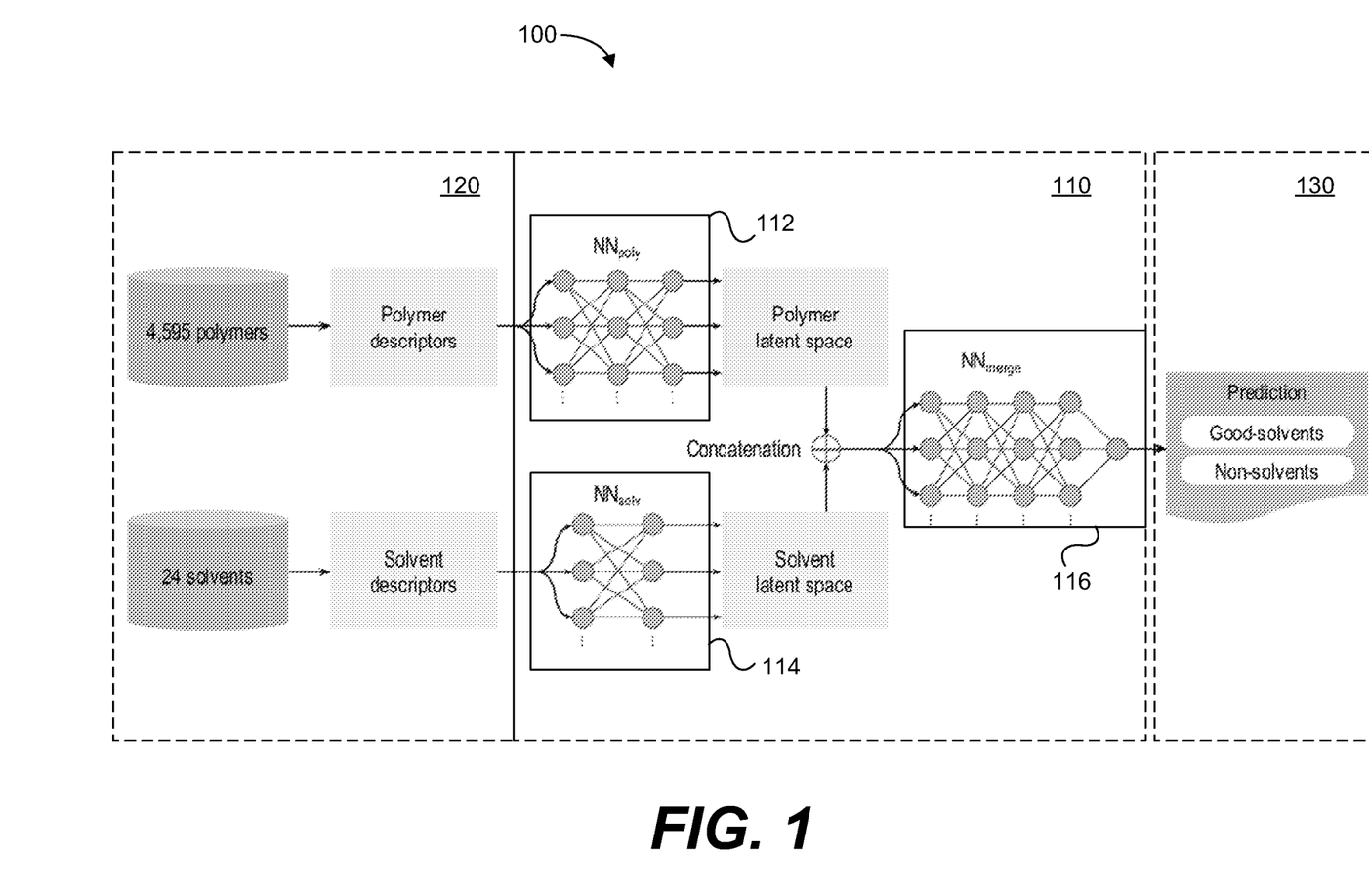
FIG. 1 illustrates a system diagram of a polymer property prediction system according to some examples of the present disclosure.

FIG. 1 illustrates a schematic of an example polymer prediction system 100. As shown, the system 100 can include a deep learning neural network 110. The deep learning neural network 110 can include one or more branches, such as a polymer branch 112 and a property branch 114. The property branch 114 can correspond to any property of the polymer, such as the solubility of the polymer in a solvent. The deep learning neural network 110 can also include a merged layer 116 resulting from the concatenation of the polymer branch 112 and the property branch 114. The concatenation can be performed by a concatenation operation 118.

The property branch 114 can comprise any number of hidden layers, each with a plurality of neurons. The polymer branch 112 can comprise any number of layers, each with a plurality of neurons. It is to be understood that any number of neurons can be used as desired. In some examples, the final hidden layer of the property branch 114 can comprise a plurality of neurons and be designated as a property latent space. Similarly, the final layer of the polymer branch 112 can comprise a plurality of neurons and be designated as a polymer latent space. All of the hidden layers in the deep learning neural network 110 can be constructed with the parameterized rectified linear unit activation function. The parameterized rectified linear unit (PRelu) can be a function of the form $f(x)=a*x$ for $x<0$ and $f(x)=x$ for $x>0$. The parameter "a" can be learned by the deep learning neural network 110. Alternatively, or additionally, the hidden layers can be constructed with any activation function, such as PReLu, ReLu, LeakyReLu, and the like.

The system 100 can also include a training dataset 120. The training dataset 120 can include a plurality of polymers and their corresponding known properties. For example, the training dataset 120 can comprise a plurality of polymer-solvent pairs and polymer-non-solvent pairs. The chemical and structural features of the polymers in the training dataset 120 can be encoded in terms of a numerical vector, and the corresponding properties (solvents, in this example), can be represented using one-hot encoding, which can be another numerical vector with binary (0 or 1) labels indicating which solvent (or, in the general case, which property) is being considered. The training dataset 120 can then be used to train the deep learning neural network 110.

The system 100 can also include a user interface 130. The user interface 130 can be capable of displaying and receiving information and data to a user of the system 100. For instance, the user interface 130 can receive an input from a user, and the input can comprise a first polymer having a first set of functional groups. The system 100 can then analyze the first polymer using the deep learning neural network 110. Using similar chemical and structural features to polymers from the training dataset 120, the system 100 can determine the properties of the first polymer. For example, a non-solvent for the first polymer can be determined by analyzing polymers from the training dataset 120 that have similar chemical and structural properties. The system 100 can therefore determine a value indicative of a property for the first polymer. For example, a value of 1 can indicate a good solvent for the first polymer, whereas a value of 0 can indicate a non-solvent for the first polymer. In some examples, the property and the value can then be output to the user via the user interface 130.

In some examples, the system 100 can also determine if the value is above or below a predetermined threshold. By way of the solubility example, a value above 0.5 can indicate a good solvent, whereas a value below 0.5 can indicate a non-solvent. To aid in determining the value, the merged layer 116 can include a sigmoid activation function. The sigmoid activation function can have the form $f(x)=1/1+\exp(-x)$. The range of the function can be between 0 and 1. The sigmoid activation function can be a standard function used for neural network classification models. The activation value of the sigmoid activation function can correspond to the predetermined threshold. In some examples, the merged layer 116 can comprise a set of hidden layers. The sigmoid activation function can be present in the final layer of the set of hidden layers.

Figure 2:
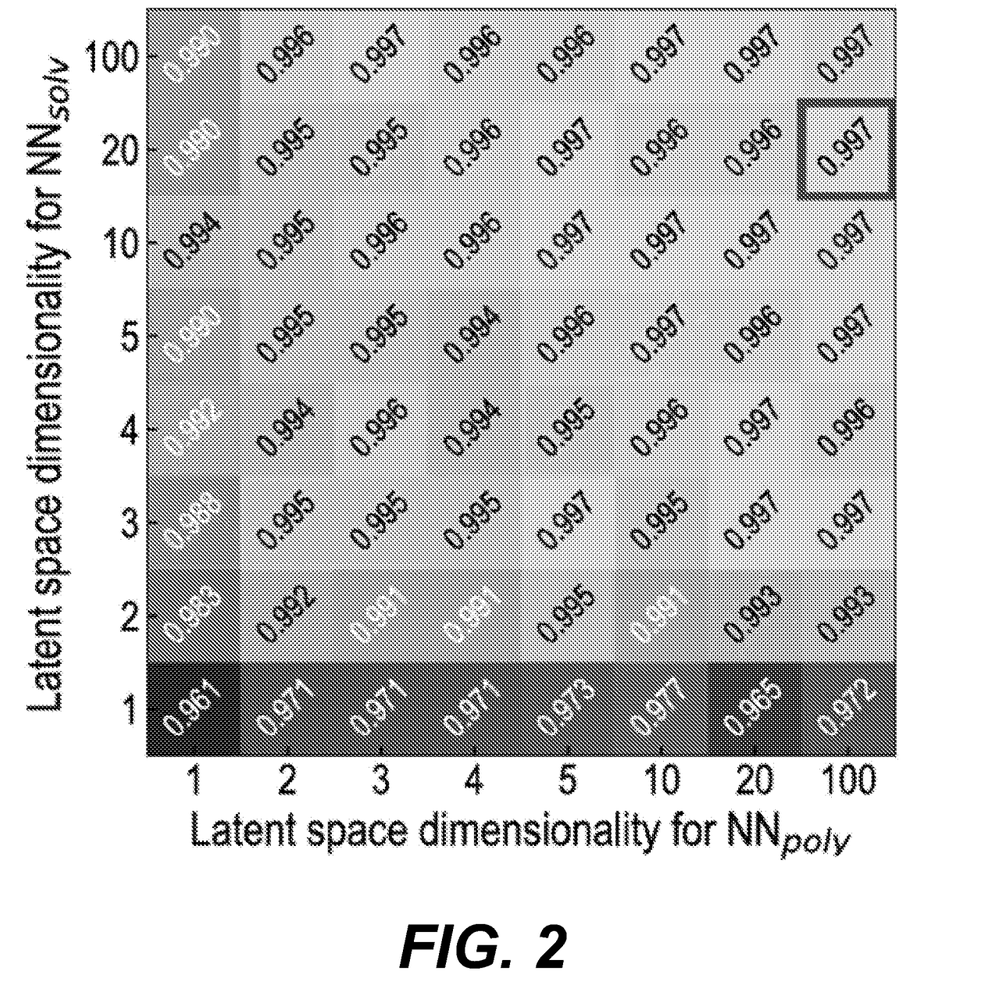
FIG. 2 illustrates a chart of the accuracy of a polymer property prediction system for various latent space dimensionalities according to some examples of the present disclosure.

The accuracy of the deep learning neural network 110 can depend on the latent space dimensionality of the polymer branch 112 and the property branch 114. For example, if solubility is the desired property, it is understood that the Hildebrand and Hansen solubility criteria posses a dimensionality of one and three, respectively. As shown in FIG. 2, the accuracy of the presently disclosed system saturates at about 99.7. As shown, a dimensionality from 3 to 5 can be sufficient in the construction the system 100 with exceptional accuracy for this particular property. For greater accuracy, the outlined model can be chosen to a greater dimensionality, as shown.

Figure 3:
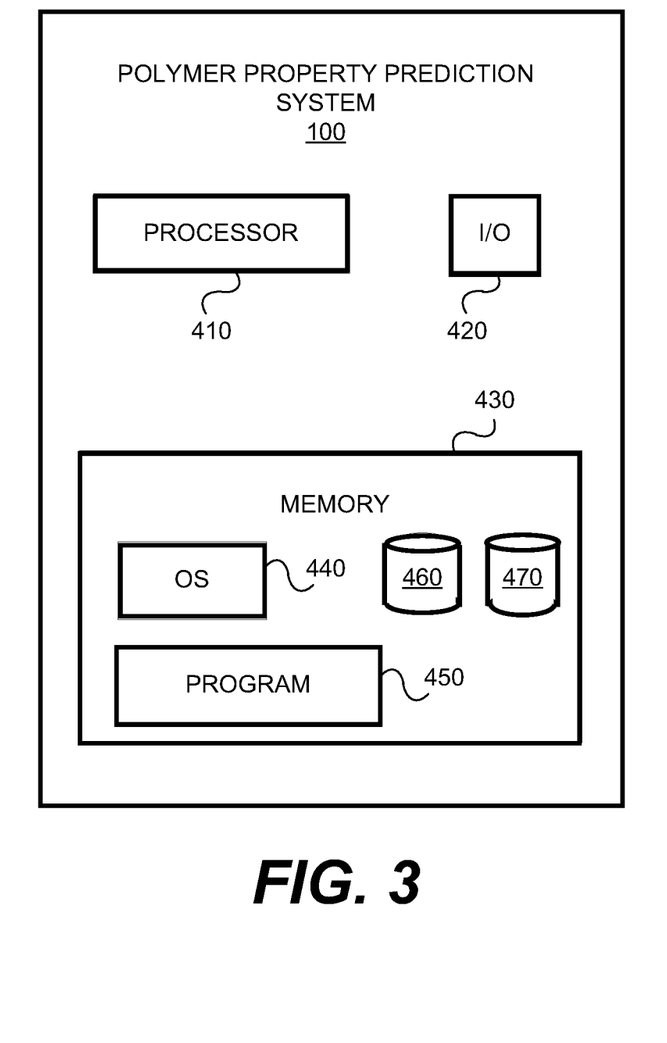
FIG. 3 illustrates an example computing device used to execute the disclosed polymer property prediction systems and methods.

An example of a polymer property prediction system 100 is shown in more detail in FIG. 3. As shown, the polymer property prediction system 100 can include a processor 310; an input/output (I/O) device 320; a memory 330, which can contain an operating system (OS) 340; a storage device 360, which can be any suitable repository of data; and a program

350. In some examples, the polymer property prediction system 100 can also include a communication interface, such as a transceiver. In some examples, the polymer property prediction system 100 can further include a peripheral interface, a mobile network interface in communication with the processor 310, a bus configured to facilitate communication between the various components of the polymer property prediction system 100, and/or a power source configured to power one or more components of the polymer property prediction system 100. In certain examples, the polymer property prediction system 100 can include a geographic location sensor (GLS) for determining the geographic location of the biometric measurement device.

While the following methods may be described with reference to the polymer property prediction system 100, it is understood that one or more method steps or whole methods can be performed by other constructions of the polymer property prediction system 100, other systems, general-purpose computers, computer operators, and the like.

Figure 4:
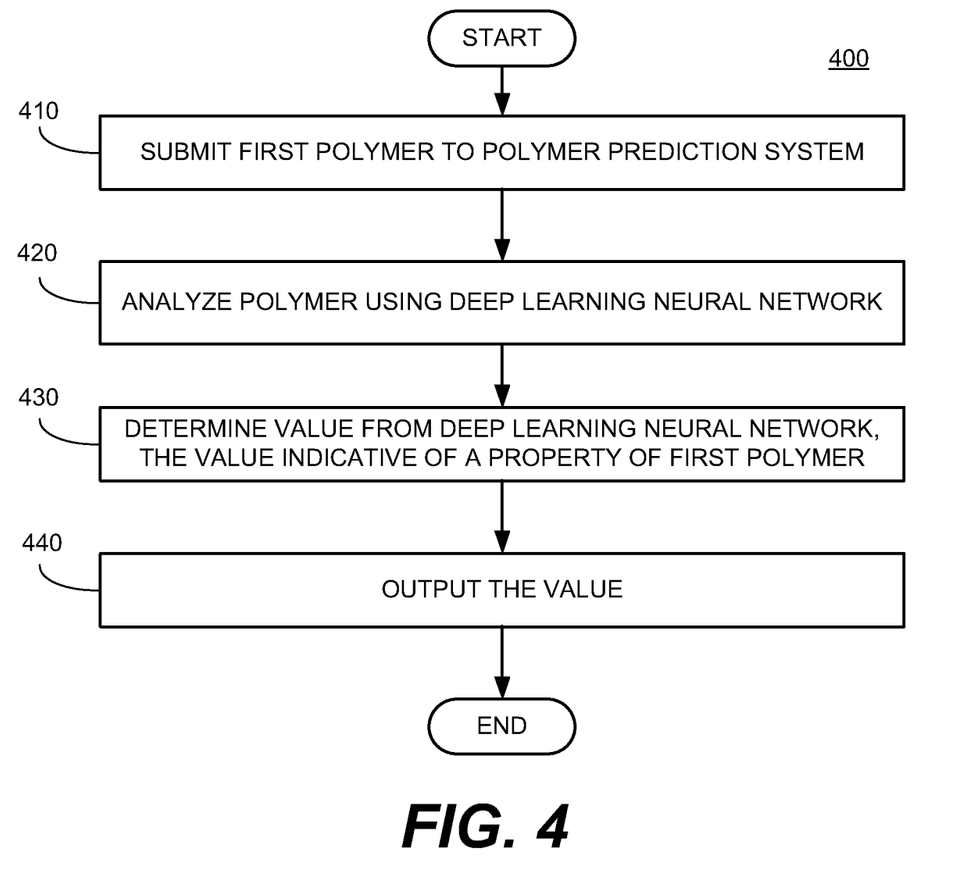
FIG. 4 illustrates a flow chart of a method for predicting polymer properties according to some examples of the present disclosure.

FIG. 4 illustrates a flowchart of a method 400 for predicting polymer properties. In block 410, a first polymer can be submitted to a polymer prediction system (such as the polymer prediction system 100). The first polymer can have a first set of functional groups. The first polymer can be submitted through the user interface 130. The user interface 130 can provide additional data to the user and receive additional information from the user. The user interface 130 can include a display screen. The method can then proceed to block 420 or on to other method steps not shown.

In block 420, the first polymer can be analyzed using the deep learning neural network 110 to analyze the first set of functional groups. The deep learning neural network 110 can include some or all of the components of the deep learning neural network 110. For example, the polymer branch 112 can analyze the first polymer while the property branch 114 analyzed good solvents and non-solvents for the first polymer. The method can then proceed to block 430 or on to other method steps not shown.

In some examples, the method 400 can also include training the deep learning neural network 110. The deep learning neural network 110 can be trained using a training dataset comprising a plurality of known polymers and a plurality of descriptors for each of the plurality of known polymers.

In block 430, a value can be determined from the merged layer 116. The value can be indicative of a property of the first polymer, such a solubility. The value can be determined to be above or below a predetermined threshold. For example, a value above a predetermined threshold can indicate a good solvent, whereas a value below a predetermined threshold can indicate a nonsolvent. The value can also simply be outputted to the user, e.g., displayed to a user on a computer display, to allow the user to further analyze the value. The method can then proceed to block 440 or on to other method steps not shown.

In block 440, the value can be output through the user interface 130. The value can also be displayed using various charts, plots, graphs, and the like to help the user visualize the data. The method can then terminate or proceed on to other method steps not shown.

As used in this application, the terms "component," "module," "system," "server," "processor," "memory," and the like are intended to include one or more computer-related units, such as but not limited to hardware, firmware, a combination of hardware and software, software, or software in execution. For example, a component may be, but is not limited to being, a process running on a processor, an object, an executable, a thread of execution, a program, and/or a computer. By way of illustration, both an application running on a computing device and the computing device can be a component. One or more components can reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system, and/or across a network such as the Internet with other systems by way of the signal.

Certain embodiments and implementations of the disclosed technology are described above with reference to block and flow diagrams of systems and methods and/or computer program products according to example embodiments or implementations of the disclosed technology. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, may be repeated, or may not necessarily need to be performed at all, according to some embodiments or implementations of the disclosed technology.

These computer-executable program instructions may be loaded onto a general-purpose computer, a special-purpose computer, a cloud computing network of remote servers, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks.

As an example, embodiments or implementations of the disclosed technology may provide for a computer program product, including a computer-usable medium having a computer-readable program code or program instructions embodied therein, said computer-readable program code adapted to be executed to implement one or more functions specified in the flow diagram block or blocks. Likewise, the computer program instructions may be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special-purpose hardware and computer instructions.

Certain implementations of the disclosed technology are described above with reference to computing devices may include mobile computing devices. Those skilled in the art recognize that there are several categories of mobile devices, generally known as portable computing devices that can run on batteries but are not usually classified as laptops. For example, mobile devices can include, but are not limited to portable computers, tablet PCs, internet tablets, PDAs, ultra-mobile PCs (UMPCs), wearable devices, and smart phones. Additionally, implementations of the disclosed technology can be utilized with internet of things (IoT) devices, smart televisions and media devices, appliances, automobiles, toys, and voice command devices, along with peripherals that interface with these devices.

While the present disclosure has been described in connection with a plurality of exemplary aspects, as illustrated in the various figures and discussed above, it is understood that other similar aspects can be used, or modifications and additions can be made to the described aspects for performing the same function of the present disclosure without deviating therefrom. For example, in various aspects of the disclosure, methods and compositions were described according to aspects of the presently disclosed subject matter. However, other equivalent methods or composition to these described aspects are also contemplated by the teachings herein. Therefore, the present disclosure should not be limited to any single aspect, but rather construed in breadth and scope in accordance with the appended claims.

EXAMPLES

The following exemplary use cases describe examples of a typical user flow pattern. They are intended solely for explanatory purposes and not limitation.

Numerous descriptors can be utilized, and these descriptors can be broadly categorized into 4 structural hierarchies. The first family of descriptors includes the so-called atomic-triples fingerprint and the second family of descriptors can be obtained from the open-source cheminformatics package RDKit. The third family of descriptors can be obtained by searching for commonly occurring substructures/blocks in this large polymer dataset. Finally, a set of polymer-chain specific descriptors can be included to encode certain higher-level features such as the length of the side chain, number of rings in the main chain, etc. All the descriptors can be modified to take into account the one-dimensional periodicity of large-molecular weight polymer chains. For instance, all the fingerprint components can be normalized with respect to the number of atoms in the polymer repeat unit.

The disclosed systems and methods can utilize one-hot encoding to represent each of the properties. One-hot encoding can be a technique to represent categorical variables using a binary representation. The fingerprint vector can have as many components as there are properties to be determined, and the particular property of interest can correspond to a coding one in the corresponding fingerprint component and all other fingerprint components will be set to 0.

A slightly modified version of the multilayer perceptron neural network algorithm can be utilized for the particular example of binary classification (good-solvent or non-solvent) problem. The neural network, as depicted in FIG. 1 consists of two input branches, one for the solvent fingerprints and the other for the polymer descriptors. The solvent branch of the neural network (NNsolv) consists of 2 hidden layers, each with 20 neurons, and the polymer branch of the neural network (NNpoly) consists of 3 layers, each with 100 neurons. The final hidden layer of the solvent branch of the neural network consists of 20 neurons and can be labelled as the 'Solvent Latent Space' in FIG. 1. Similarly, the final layer of the polymer branch of the neural network consisted of 100 neurons and can be labelled as the 'Polymer Latent Space'. The Solvent Latent Space and Polymer Latent Space hidden layers can be merged using a concatenation operation and passed on to a final set of hidden layers (NNmerge). All the hidden layers in the neural network can be constructed with the parameterized rectified linear unit (PReLU) activation function. The final layer consists of a single neuron with the sigmoid activation function wherein an ideal good solvent can be denoted by an activation value of '1' and an ideal non-solvent can be denoted by an activation value of '0'. The threshold to differentiate between a non-solvent and a good solvent can be set at 0.5.

Most of the 24 solvents considered in this study displayed a highly imbalanced class distribution. For instance, as shown in Table S2, there can be 2,131 polymers for which methanol can be considered a non-solvent but only 148 polymers for which methanol can be a good solvent. Therefore, for the case of methanol, the dataset can be upsampled to include an equivalent number of polymers for which methanol can be a good solvent. This procedure can be repeated for each one of the 24 solvents and thus ensured an almost equivalent number of cases of good-solvent and non-solvent classifications.

Following the dataset upsampling a randomized 90%/10% train/test split can be utilized, and 5-fold cross validation can be further performed on the training set. During the 5-fold cross validation, the validation set was utilized to determine the optimal number of epochs for each fold. The 'Adam' gradient descent method can be utilized for training the neural network weights along with a training batch-size of 100.

As mentioned earlier, the disclosed systems and methods can be benchmarked against existing methods for determining solubility. For this purpose, the Hildebrand criteria can be used, since it is not only widely utilized, but it is also the only solubility parameter that is available for a considerable number of polymers. A dataset of 113 polymer Hildebrand parameters from the dataset sources can be analyzed. The polymer fingerprints can be obtained for the polymers, and Gaussian Process Regression using the radial basis function (RBF) kernel can be utilized to map the polymers to their associated Hildebrand solubility parameters. Through this process, the disclosed systems and methods can obtain a machine learning model to predict the solubility parameter of all the polymers in our dataset of 4,595 polymers. For the case of the 24 solvents, the Hildebrand parameter was readily available from multiple sources in literature. Following the standard procedure, if the absolute value of the difference in Hildebrand parameters of the solvent and polymer was less than 2 $MPa^{1/2}$, the solvent was classified as a good solvent for that particular polymer. If the difference was greater than 2 $MPa^{1/2}$, the solvent was classified as a non-solvent for that polymer.

Figure 5:
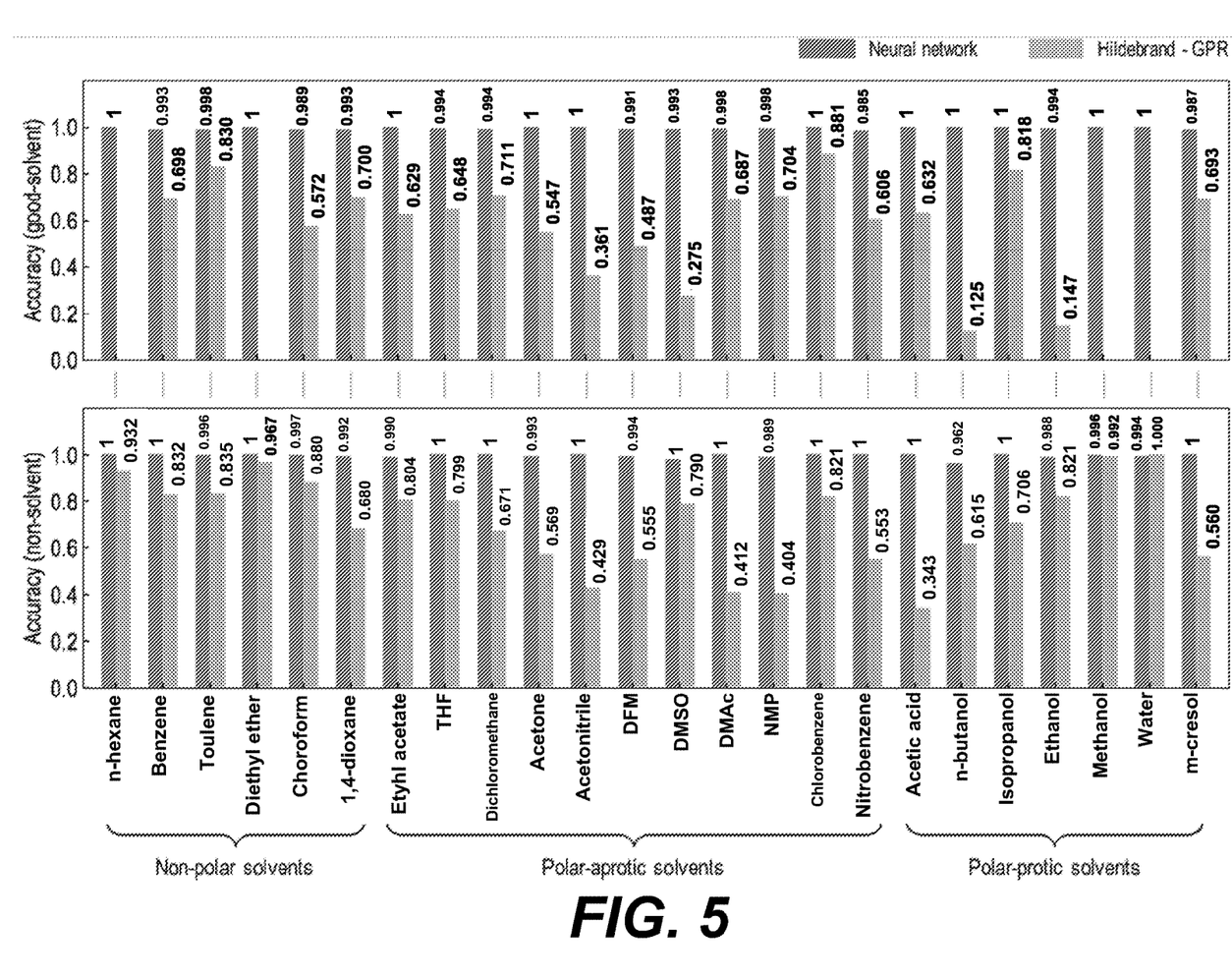
FIG. 5 illustrates an example of solubility prediction for a plurality of polymers compared to the prediction of the Hildebrand model.

In contrast to the neural network, the Hildebrand solubility criterion when applied to this large polymer dataset displayed a good-solvent classification accuracy of only 50% and a non-solvent classification accuracy of 70%. The non-solvent classification accuracy can be superior to that of the good-solvent classification since it can be a simple criterion of exclusion. As shown in FIG. 5, the performance of the Hildebrand model can be significantly inferior with respect to solubility prediction for polar-protic solvents like water, methanol and ethanol. However, surprisingly, it also performs poorly for non-polar solvents, such as n-hexane and diethyl ether. The two solvents possess Hildebrand parameters of 14.9 and 15.4 $MPa^{1/2}$, respectively. This dataset bias can be reflected in the poor predictive capabilities for the solvents n-hexane and diethyl ether.

What is claimed is:

1. A method for predicting polymer properties comprising:
    analyzing a first polymer using a deep learning neural network to analyze a first set of functional groups of the first polymer, the deep learning neural network comprising a merged layer formed from the concatenation of a property branch and a polymer branch;
    determining a value from the merged layer; and
    outputting the value.

2. The method of claim 1 further comprising submitting the first polymer to a polymer prediction system;
    wherein the polymer prediction system comprises the deep learning neural network;
    wherein the determined value is indicative of a property of the first polymer;
    wherein outputting the value comprises outputting the value to a user of the polymer prediction system;
    wherein the property branch is a solubility branch; and
    wherein the property is a solubility of the first polymer in a first solvent.

3. The method of claim 2, wherein the value is indicative of the first solvent being a good solvent.

4. The method of claim 2, wherein the value is indicative of the first solvent being a nonsolvent.

5. The method of claim 2, wherein the determining further comprises determining;
    if the value is above a first predetermined threshold; and
    if the value is below a second predetermined threshold.

6. The method of claim 1 further comprising training the deep learning neural network using a training dataset comprising a plurality of known polymers and a plurality of descriptors for each of the plurality of known polymers.

7. The method of claim 1, wherein the property branch comprises two or more layers, each layer having from 1 to 100 neurons.

8. The method of claim 1, wherein the polymer branch comprises two or more layers, each layer having from 1 to 100 neurons.

9. The method of claim 1, wherein:
    one or both:
        the property branch comprises two or more layers; and
        the polymer branch comprises two or more layers;
    each layer has from 1 to 100 neurons; and
    each layer is constructed with a parameterized rectified linear unit.

10. The method of claim 1, wherein the merged layer comprises a sigmoid activation function.

11. A deep learning neural network comprising:
    a property branch comprising two or more layers, each layer having a plurality of neurons;
    a polymer branch comprising two or more layers, each layer having a plurality neurons; and
    a merged layer including a concatenation operation, the concatenation operation configured to concatenate the property branch and the polymer branch.

12. A polymer prediction system comprising:
    the deep learning neural network of claim 11;
    wherein the deep learning neural network further comprises a training dataset comprising a plurality of known polymers and a plurality of descriptors for each of the plurality of known polymers; and
    wherein the system is configured to:
        receive an inputted first polymer having a first set of functional groups;
        analyze the first polymer using the deep learning neural network;
        determine a value for the first polymer, the value being indicative of a property of the first polymer; and
        output the property and the value to a user of the polymer prediction system.

13. The system of claim 12, wherein the property branch is a solubility branch; and
    wherein the property is a solubility of the first polymer in a first solvent.

14. The system of claim 12, wherein the value is indicative of the first solvent being a good solvent.

15. The system of claim 12, wherein the value is indicative of the first solvent being a nonsolvent.

16. The system of claim 12, wherein the system is further configured to determine;
    if the value is above a first predetermined threshold; and
    if the value is below a second predetermined threshold.

17. The deep learning neural network of claim 11, wherein each of the two or more layers in the property branch are constructed with a parameterized rectified linear unit.

18. The deep learning neural network of claim 11, wherein each of the two or more layers in the polymer branch are constructed with a parameterized rectified linear unit.

19. The deep learning neural network of claim 11, wherein the deep learning neural network has a latent space dimensionality selected from 3 to 10.

20. The deep learning neural network of claim 11, wherein the merged layer further comprises a sigmoid activation function.

* * * * *